US008091436B2

(12) United States Patent  
Eckhardt et al.

(10) Patent No.: US 8,091,436 B2  
(45) Date of Patent: *Jan. 10, 2012

(54) DIFFERENTIAL FORCE SENSOR

(75) Inventors: Todd Eckhardt, Westerville, OH (US); Richard Wade, Worthington, OH (US); Ryan Jones, Dublin, OH (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,321

(22) Filed: Jul. 12, 2010

(65) Prior Publication Data

US 2011/0000313 A1    Jan. 6, 2011

Related U.S. Application Data

(63) Continuation of application No. 12/256,181, filed on Oct. 22, 2008, now Pat. No. 7,775,126.

(51) Int. Cl.  
*G01F 1/37* (2006.01)  
*A61M 31/00* (2006.01)

(52) U.S. Cl. ............... 73/861.52; 73/861.47; 604/93.01; 604/67; 604/505

(58) Field of Classification Search ......................... None  
See application file for complete search history.

(56) References Cited

U.S. PATENT DOCUMENTS

| | | | |
|---|---|---|---|
| 4,395,915 A | 8/1983 | Singh | |
| 4,528,855 A | 7/1985 | Singh | |
| 4,932,045 A | 6/1990 | Kasoff et al. | |
| 5,124,960 A | 6/1992 | Miller et al. | |
| 5,136,621 A | 8/1992 | Mitchell et al. | |
| 5,656,785 A | 8/1997 | Trainor et al. | |
| 5,661,245 A | 8/1997 | Svoboda et al. | |
| 6,229,190 B1 | 5/2001 | Bryzek et al. | |
| 6,612,179 B1 | 9/2003 | Kurtz | |
| 6,945,120 B1 * | 9/2005 | Marcus et al. | 73/756 |
| 7,073,375 B2 | 7/2006 | Parker et al. | |
| 7,077,008 B2 * | 7/2006 | Pham et al. | 73/716 |
| 7,162,927 B1 * | 1/2007 | Selvan et al. | 73/753 |
| 7,296,479 B2 | 11/2007 | Hogeland | |
| 7,320,253 B2 | 1/2008 | Hanazawa et al. | |
| 7,559,252 B2 | 7/2009 | Schadler et al. | |

(Continued)

OTHER PUBLICATIONS

U.S. Appl. No. 12/834,260, filed Jul. 12, 2010.  
Kremer et al., "Signal Conditioning Circuits for Sensors Frame ASICs or Modular Signal Conditioning," 8 pages, Analog Microelectronics, Aug. 2000.

(Continued)

*Primary Examiner* — Harshad Patel  
(74) *Attorney, Agent, or Firm* — Seager, Tufte & Wickhem LLC (57) ABSTRACT

A differential force sensor method and apparatus for automatically monitoring manual injections through an intravenous line. The differential force sensor includes two piezoresistive sense die that are packaged in close proximity utilizing a number of packaging processes. The two piezoresistive sense die can be utilized to measure forces exerted on a diaphragm on either side of an orifice. The piezoresistive sense die can be packaged in close proximity to make intimate contact with the diaphragms on either side of the orifice. The differential force sensor further includes two plungers that make intimate contact with the diaphragm and transfer the force into the piezo-resistive sense dies. Additionally, one or more ASICs and microcontrollers can be utilized to provide thermal calibration and differential calculation.

20 Claims, 7 Drawing Sheets

U.S. PATENT DOCUMENTS

| | | | |
|---|---|---|---|
| 7,775,126 B2 * | 8/2010 | Eckhardt et al. | 73/861.52 |
| 7,775,127 B2 * | 8/2010 | Wade | 73/861.52 |
| 2008/0114256 A1 | 5/2008 | Zhang et al. | |
| 2010/0100052 A1 | 4/2010 | Eckhardt et al. | |
| 2010/0160893 A1 | 6/2010 | Wade | |

OTHER PUBLICATIONS

Honeywell, "Force Sensors, FSG and FSL Series," 23 pages, 2003.
Honeywell, "Pressure Sensors, FS01/FS03 Force Sensors," 4 pages, 2003.

* cited by examiner

FIG. 9 ly monitoring manual injections through an IV line. Also, a need exits for a small-sized and lightweight differential force sensor that is capable of being utilized in close proximity to the injection point in a patient's body to reduce patient discomfort.

DIFFERENTIAL FORCE SENSOR

This application is a continuation of U.S. patent application Ser. No. 12/256,181, filed Oct. 22, 2008 now U.S. Pat. No. 7,775,126, and entitled "DIFFERENTIAL FORCE SENSOR", which is incorporated herein by reference.

TECHNICAL FIELD

Embodiments are generally related to sensor methods and systems. Embodiments are also related to differential force sensors. Embodiments are additionally related to differential force sensors utilized in the context of monitoring manual patient injections through an intravenous line.

BACKGROUND OF THE INVENTION

In the medical field, it is common for intravenous (IV) medications such as, for example, antibiotics, antiviral, antiemetic, chemotherapy, and so forth, to be administered intermittently with a frequency as often as multiple times per day. Depending on the frequency of administration, the patient is either repeatedly connected to and disconnected from an IV line or is continuously connected to an IV line between administrations. In either case, the intermittent medications are generally administered by trained personnel utilizing predefined procedures that often include a series of manual steps and a large number of disposable supplies. Each manual step in such procedures increases the risks associated with multiple manipulations and entry of IV sites.

Patient injections through IV lines can be currently recorded manually. The nurse administering the medication must follow strict guidelines regarding the quantity of medication to be administered and potentially the rate at which the medication should be administered. Also, regular monitoring of infusion sites assists in reducing the severity of adverse effects when infiltration and extravasations occur. Hence, an automated method for monitoring manual injections through an IV line is desired.

Based on the foregoing, it is believed that a need exists for an improved differential force sensor for automatically monitoring manual injections through an IV line. Also, a need exits for a small-sized and lightweight differential force sensor that is capable of being utilized in close proximity to the injection point in a patient's body to reduce patient discomfort.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensor method and apparatus.

It is another aspect of the present invention to provide for an improved differential force sensor apparatus capable of automatically monitoring manual injections through an IV line.

The aforementioned aspects and other objectives and advantages can now be achieved as described herein. A differential force sensor apparatus and method for automatically monitoring manual injections through an intravenous line is disclosed. The differential force sensor includes two piezoresistive sense die packaged in close proximity utilizing any one of a number of packaging processes. The two piezoresistive sense die can be utilized to measure force exerted on a diaphragm on either side of an orifice. The piezoresistive sense die can be packaged in close proximity to make intimate contact with a diaphragm(s) located on either side of the orifice. The differential force sensor further includes one or more plungers that make intimate contact with the diaphragm and transfer the force to the piezoresistive sense die. Additionally, one or more ASIC components and microcontrollers can be utilized to provide thermal calibration and differential calculation.

In one embodiment, each piezoresistive sense die can be packaged utilizing a conductive seal stack, which includes a conductive seal and an environmental seal. The conductive seal stacks can be placed on a PCB (Printed Circuit Board) and held captive by a single piece of plastic housing. The single plastic housing includes, for example, two plungers that make intimate contact with the flow diaphragm and transfer the force into the piezoresistive sense die.

In a second embodiment, each piezoresistive sense die associated with the differential force sensor can be glued to a PCB. A housing can be positioned over the piezoresistive sense die, whereby a gel is then dispensed and cured into an orifice formed above the piezoresistive sense die in order to make intimate contact with the topside of the sense die. The diaphragm and the plunger can be placed on top of the gel. The force from an external diaphragm can be transmitted through the plunger and into the gel and finally into the piezoresistive sense die.

In a third embodiment, each piezoresistive sense die associated with the differential force sensor can be glued to a carrier. The gel can be dispensed into an orifice in the carrier which allows the gel to make intimate contact with the backside (e.g., etched side) of the sense die. A carrier assembly can be glued to a PCB so that the sense die is then electrically connected. The diaphragm can be placed over the cured gel and a cover is located over the system to maintain the diaphragm in place and provide an environmental seal. The signal compensation for the differential force sensor can be performed in two ASICS (one for each piezoresistive sense die) and the microcontroller can be utilized to communicate with external electronics. Note that any combination of the above embodiments may also be used, such as, for example, a sense die glued to a PCB, wherein as a ball bearing makes intimate contact with the sense die diaphragm, the force is transmitted to the ball bearing, and so forth.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
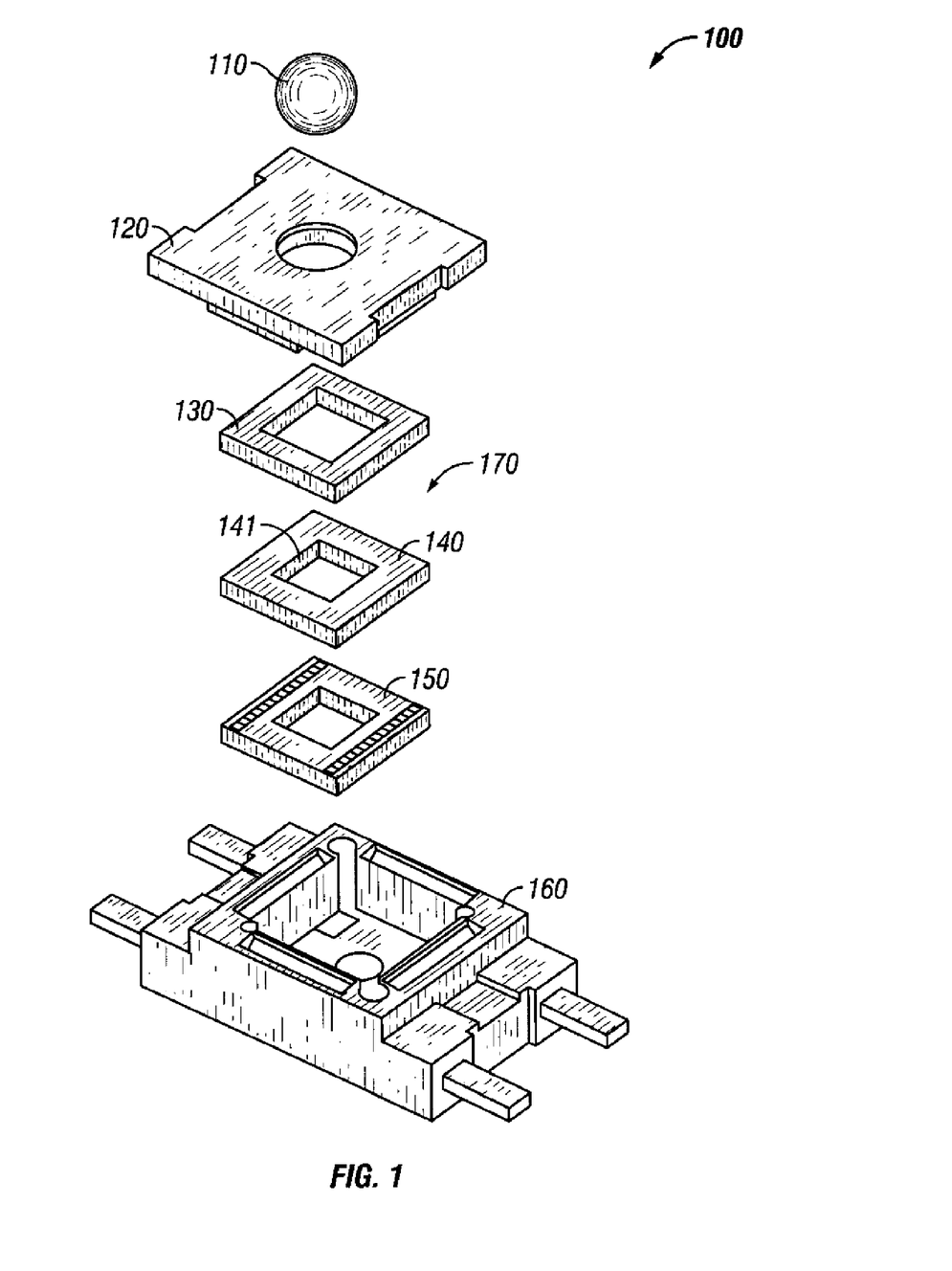
FIG. 1 illustrates an exploded view of a force sensor with piezo-resistive sense die packaged by means of conductive seal stack, in accordance with a first embodiment.

FIG. 1 illustrates an exploded view of a force sensor 100 having a piezoresistive sense die 140 packaged utilizing a conductive seal stack 170, in accordance with a preferred embodiment. As illustrated in FIG. 1, the conductive seal stack 170 generally includes a conductive seal 150 and an environmental seal 130. The conductive seal 150 and the piezoresistive sense die 140 can be inserted into a housing 160 with the environmental seal 130 inserted last over the sense die 140. The active side of the die 140 can be faced down into the housing 160. A cover 120 can be assembled to the housing 160 and can be pressed into place. A ball bearing 110 can be assembled to the force sensor 100 and can be pressed into the cover 120. The sense die 140 can include a diaphragm 141 and multiple electrically conductive bond pads (not shown) therein.

The diaphragm 141 can be utilized for absorbing the pressure or force applied. The diaphragm 141 can be made of thin silicon materials in order to measure even very minute pressure. The electrically conductive bond pads of the sense die 140 can be electrically connected to the diaphragm 141 in order to output electrical signals. Furthermore, the diaphragm 141 can be incorporated with piezoresistive elements (not shown) that convert the deformation of the diaphragm 141 due to the applied force into electrical signals utilizing well-known piezoresistive principles in order to compute the pressure in the media. The bond pads of the sense die 140 can be integrated on the piezoresistive elements. The sense die 140 can be electrically connected with the conductive elastomeric seal 150 in order to electrically connect several external electrical terminals or molded leads to the sense die 140. The housing 160 can include a set of lugs that can be utilized to snap the housing 160 and the cover 120 together. Such force sensor 100 can improve the accuracy of the sensing output signal.

Figure 2:
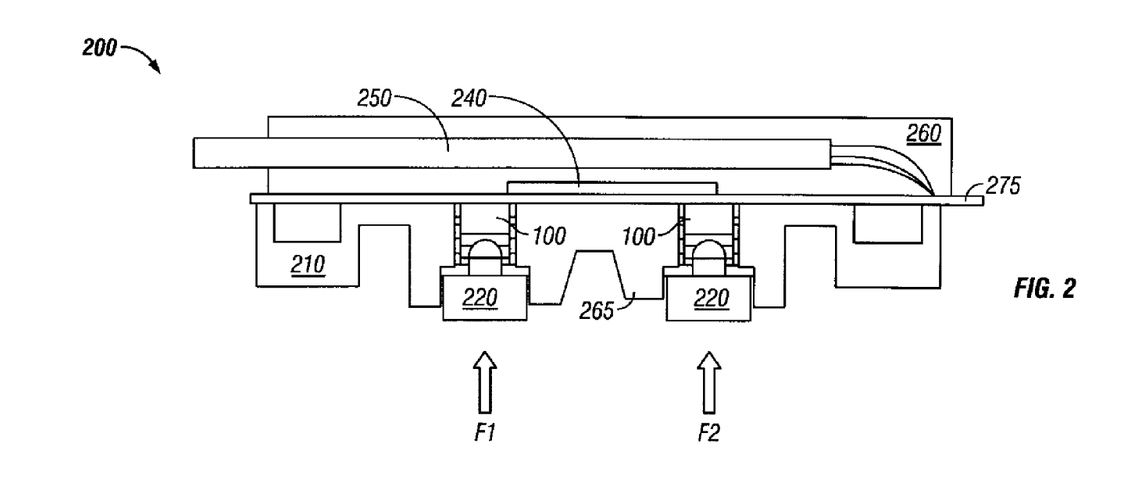
FIG. 2 illustrates a cross-sectional view of a differential force sensor with two piezoresistive sense die, each packaged by means of the conductive seal stack, in accordance with a first embodiment.

FIG. 2 illustrates a cross-sectional view of a differential force sensor 200 with two force sensors 100 each packaged by means of a conductive seal stack 170, in accordance with a first embodiment. Note that in FIGS. 1-9, identical or similar parts or elements are generally indicated by identical reference numerals. The two force sensors 100 can be packaged by means of a conductive seal stack 170, which includes the conductive seal 150 and the environmental seal 130, as depicted in FIG. 1. The force sensors 100 can be placed on a PCB (Printed Circuit Board) 275 and held captive by a single piece of plastic housing 265. The single plastic housing 265 includes two plungers 220 that make intimate contact with a flow diaphragm (not shown) and transfer the force into the piezoresistive sense die 140 associated with the force sensors 100. The differential force sensors 100 can be covered with a bottom cover 210 and a top cover 260.

Figure 3:
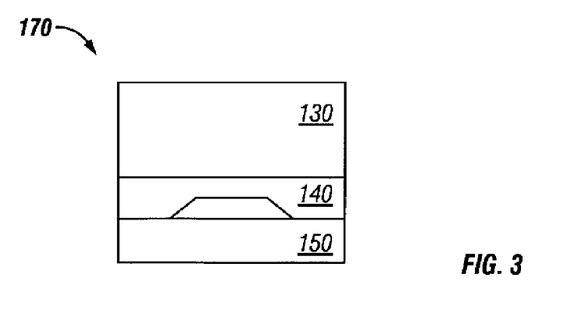
FIG. 3 illustrates an exploded view of the conductive seal stack, in accordance with a first embodiment.
Figure 9:
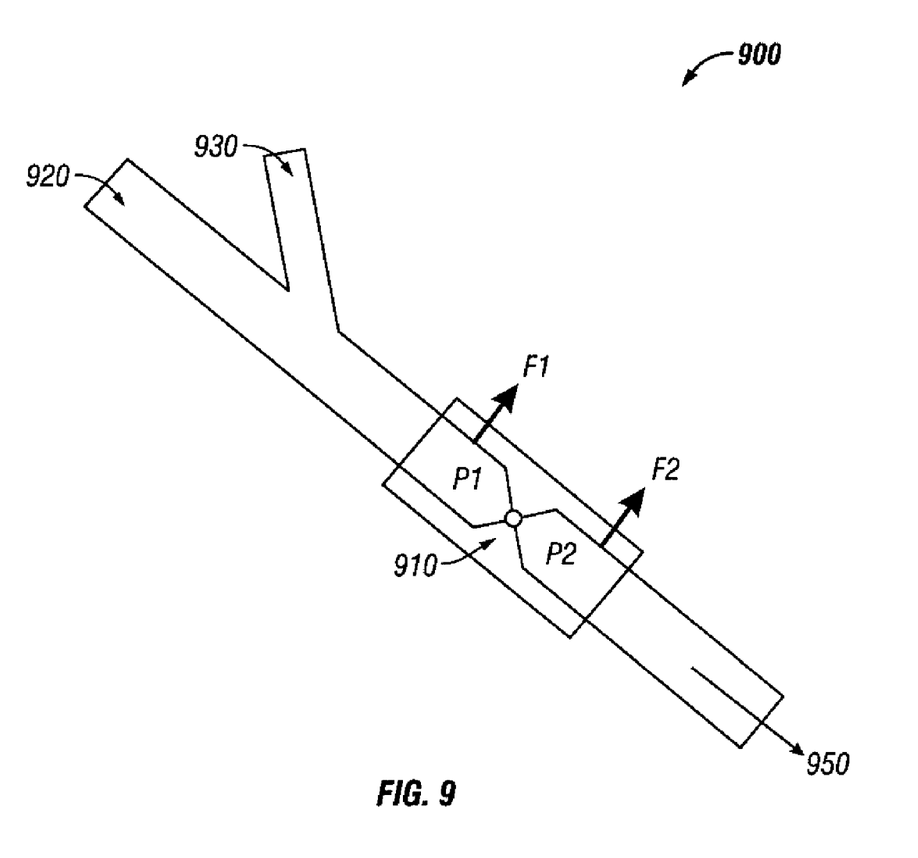
FIG. 9 illustrates a schematic diagram of an intravenous fluid delivery system utilizing differential force sensor on either side of an orifice for monitoring manual injections, which can be implemented in accordance with a preferred embodiment.

FIG. 3 illustrates an exploded view of the conductive seal stack 170. The conductive seal stack 170 comprises the conductive seal 150, the piezoresistive sense die 140 and the environmental seal 130. The two-force sensors 100 can be utilized to measure forces exerted on the diaphragm on either side of an orifice 910, as shown in FIG. 9. The two-force sensors 100 can be packaged in close proximity to make intimate contact with the diaphragms on either side of the orifice 910. The forces F1 and F2 on either side of the orifice 910 can be measured. Additionally, one or more ASICs (not shown) can be utilized to provide linearization and thermal compensation through calibration and differential calculation. A microcontroller 240 can be utilized to provide the differential calculation or flow rate calculation and communicate with external electronics through an USB cable 250.

Figure 4:
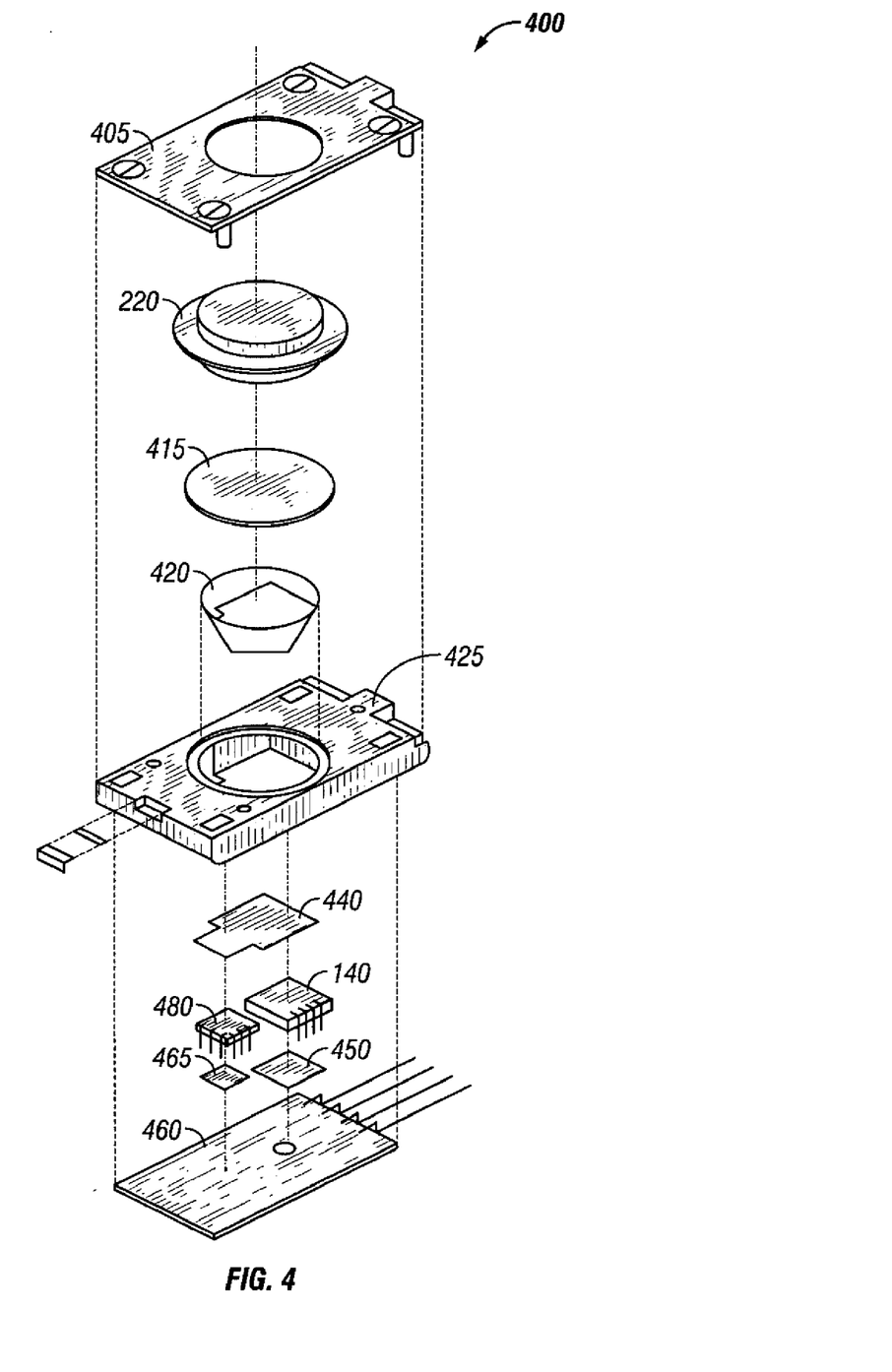
FIG. 4 illustrates an exploded view of a force sensor with piezo-resistive sense die glued to a printed circuit board (PCB), in accordance with a second embodiment.

FIG. 4 illustrates an exploded view of a force sensor 400 with piezoresistive sense die 140 glued to a printed circuit board (PCB) 460, in accordance with a second embodiment. The piezoresistive sense die 140 can be glued to the PCB 460 by means of glue 450. The differential force sensor 400 features an integrated circuit sensor element in the form of piezoresistive sense die 140 and the PCB 460 in a small plastic housing 425. Such a sensor 400 with extremely small size enables the use of multiple sensors in limited available space. Such package also provides excellent corrosion resistance and isolation to external package stress. The differential force sensor 400 comprises a dual amplifier 480 bonded to the PCB 460 utilizing an epoxy 465. A cover 405 can be placed over the sensor 400 in order to provide an environmental seal. The molded housing 425 can be positioned over the sense die 140 utilizing an epoxy 440, whereby a gel 420 can be dispensed and cured into the orifice above the sense die 140 so it makes intimate contact with the topside of the sense die 140. A Kapton diaphragm 415 and the plunger 220 can be placed on top of the gel 420.

Figure 5:
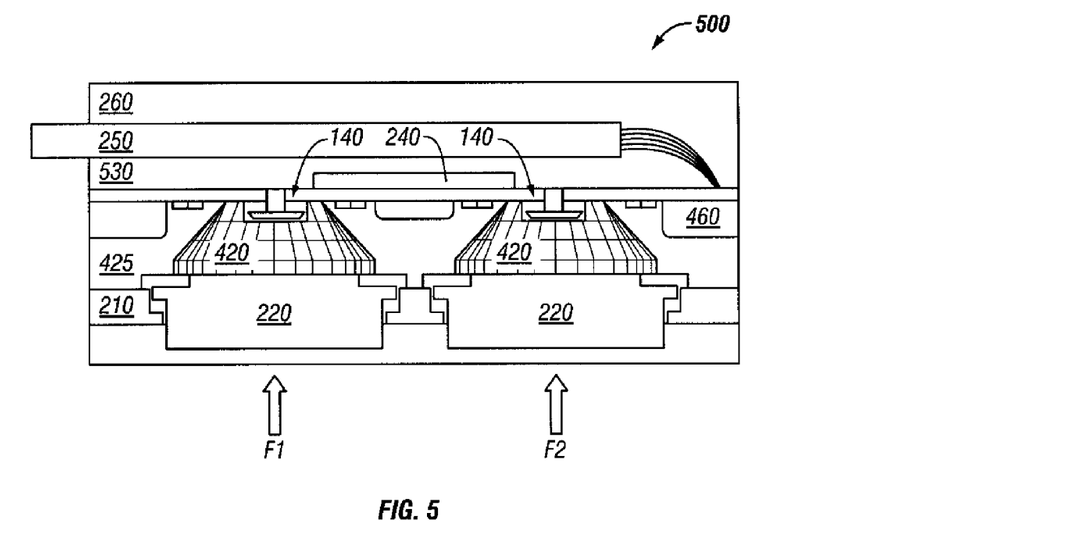
FIG. 5 illustrates a cross sectional view of a differential force sensor with two piezoresistive sense die, each glued to the PCB, in accordance with a second embodiment.

FIG. 5 illustrates a cross-sectional view of a differential force sensor 500 with two-piezoresistive sense die 140 each glued to the PCB 460, in accordance with a second embodiment. The two force sensors 500 comprising the piezo-resistive sense die 140 that are packaged in close proximity can be glued to the PCB 460. The molded housing 425 can be positioned over the sense die 140, whereby the gel 420 can be dispensed and cured into the orifice above the sense die 140 so it makes intimate contact with the topside of the sense die 140.

The diaphragm 415 and the plunger 220 can be placed on top of the gel 420. The two-piezoresistive sense die 140 can be utilized to measure forces exerted on the diaphragm 415 on either side of the orifice 910. The forces F1 and F2 from the diaphragm 415 can be transmitted through the plungers 220 and into the gel 420 and finally into the piezo-resistive sense die 140. The signal compensation for the piezoresistive sense die 140 can be completed through ASICs 530. The microcontroller 240 can be utilized to communicate with external electronics through the USB cable 250. The differential force sensor 500 can be covered with a bottom cover 210 and a top cover 260.

Figure 6:
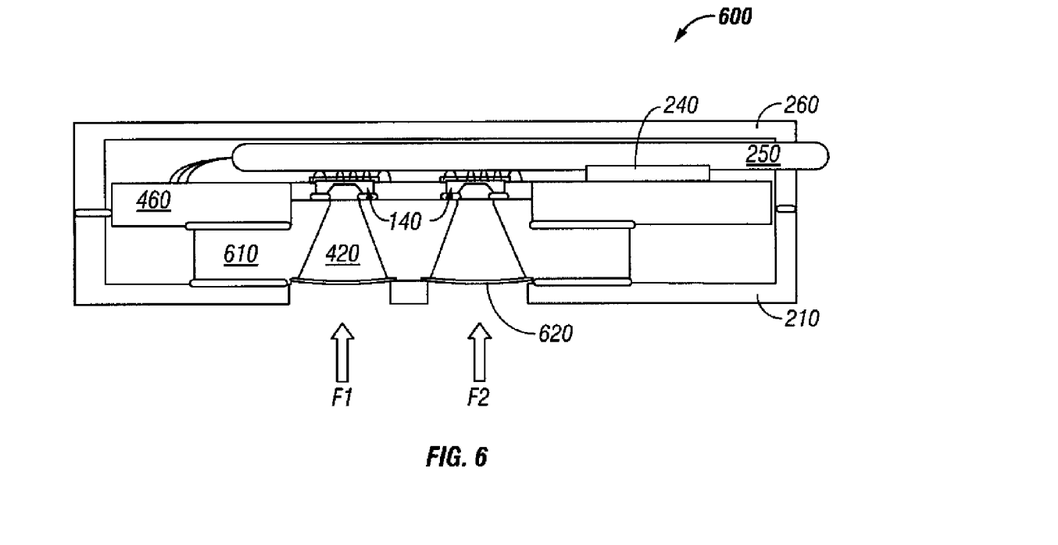
FIG. 6 illustrates a cross-sectional view of the differential force sensor with two piezoresistive sense die, each glued to a carrier, in accordance with a third embodiment.

FIG. 6 illustrates a cross-sectional view of a differential force sensor 600 with two piezoresistive sense die 140 each glued to a carrier 610, which can be implemented in accordance with a third embodiment. Again as reminder, in FIGS. 1-9 identical or similar parts or elements are generally indicated by identical reference numerals. The piezo-resistive sense die 140 can be glued to the carrier 610 and the gel 420 can be dispensed into the orifice in the carrier 610 which allows the gel 420 to make intimate contact with the back side (etched side) of the sense die 140. The carrier assembly 610 can be glued to the PCB 460 so that the sense die 140 can be electrically connected.

The diaphragm 415 can be placed over the cured gel 420 and a protective cover 620 can be placed over the gel 420 to hold the diaphragm 415 in place and provide an environmental seal. The differential force sensor 600 further comprises a top housing 260 that contains strain relief and a bottom housing 210 that holds the protective cover 620 in place. The signal compensation for the piezoresistive sense die 140 can be completed through two ASICs (not shown) and the microcontroller 240 can be utilized to communicate with external electronics through the USB cable 250.

Figure 7:
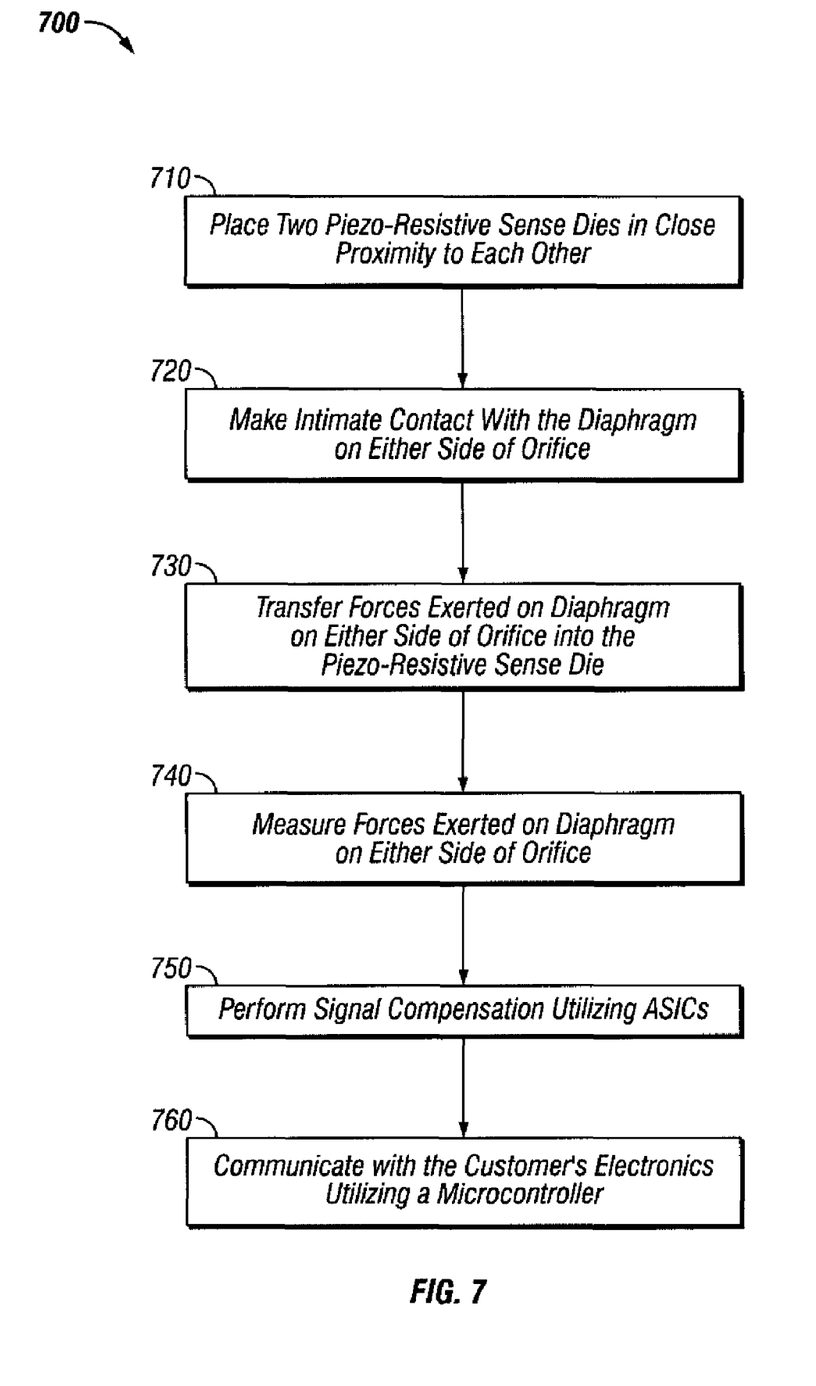
FIG. 7 illustrates a high level flow chart of operations illustrating logical operational steps of a method for automatically monitoring manual injections through an intravenous line utilizing the differential force sensor, in accordance with a preferred embodiment.

FIG. 7 illustrates a high level flow chart of operations illustrating logical operational steps of a method 700 for automatically monitoring manual injections through an intravenous line 920 utilizing the differential force sensor 200, 500 and 600, in accordance with a preferred embodiment. The two-piezoresistive sense die 140 can be packaged in close proximity utilizing a number of packaging processes, as depicted at block 710. An intimate contact can be made with the diaphragm on either side of the orifice 910, as depicted at block 720. Thereafter, forces F1 and F2 exerted on the diaphragm on either side of the orifice 910 can be transferred into the piezoresistive sense die 140, as depicted at block 730. The forces F1 and F2 exerted on diaphragm on either side of the orifice 910 can be measured, as depicted at block 740. Next, signal compensation can be performed in the ASICs, as depicted at block 750.

The microcontroller 240 can be utilized to calculate the differential force and associated flow and communicate with external electronics for further communication, as depicted at block 760. Such an automated method 700 monitors manual injections through an IV line utilizing a non-contact differential force measurement on either side of the orifice 910. The output of the differential force sensor 200, 500 and 600 can be the individual force measurements in the form of an electrical signal (i.e., digital or analog) and potentially a differential signal (i.e., the difference between the two sense elements). Additionally, the small size and lightweight of the sensor 200, 500 and 600 reduce patient discomfort possible through close proximity of the device to the injection point in the patient's body.

Figure 8:
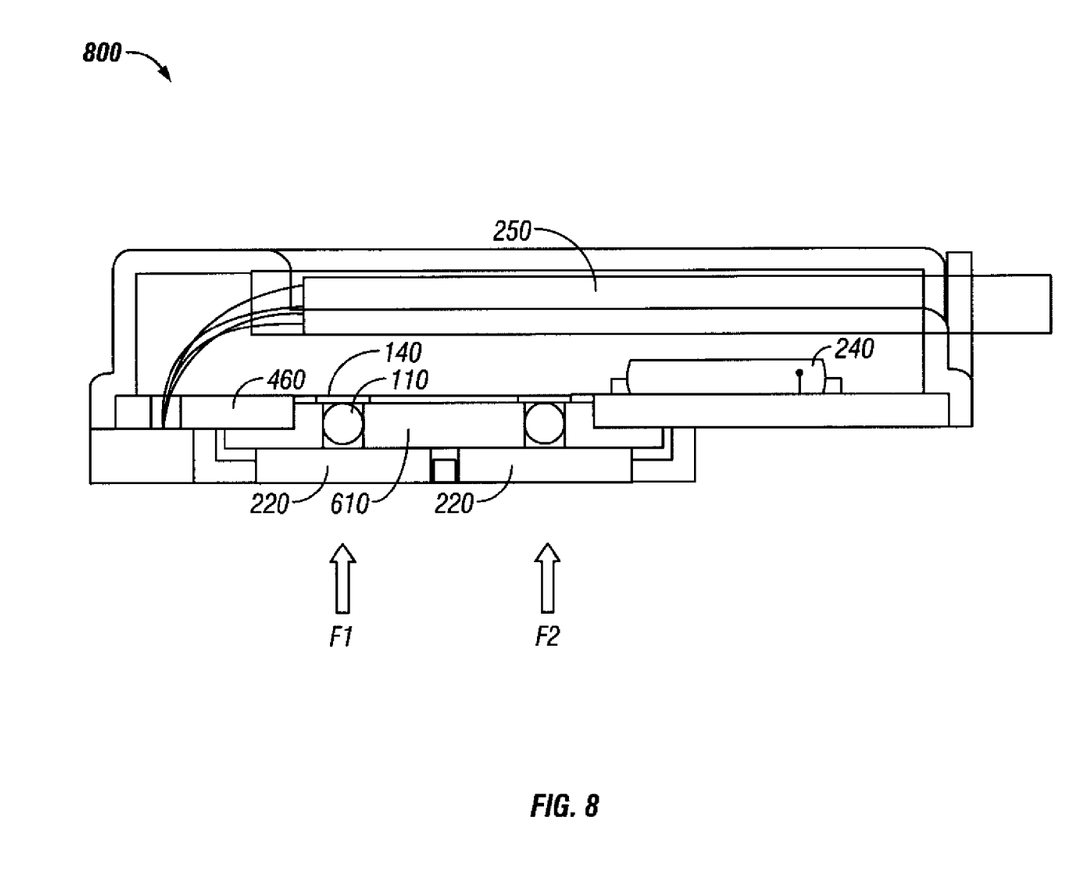
FIG. 8 illustrates a cross-sectional view of a differential force sensor glued to the carrier with mechanical contact from a ball bearing and a plunger, in accordance with a preferred embodiment.

FIG. 8 illustrates a cross-sectional view of a differential force sensor 800 glued to the carrier 610 with mechanical contact from the ball bearing 110 and the plunger 220, in accordance with a preferred embodiment. The piezo-resistive sense die 140 can be glued to the carrier 610. The force F1 and F2 can be transferred to the sense die 140 through the plunger 220 and the ball bearing 110. Note that the sense die 140 can also be attached to the PCB 460 with mechanical contact from the ball bearing 110 and/or the plunger 220. The signal compensation can be performed in two ASICs and a microcontroller 240 can be utilized to communicate with external electronics through the USB cable 250. Note that the embodiments discussed herein should not be construed in any limited sense. It can be appreciated, of course, that other types of combination of the above embodiments may also be utilized such as, for example, the sense die glued to the PCB, wherein as a ball bearing makes intimate contact with the sense die diaphragm, the force is transmitted to the ball bearing, and so forth. However, it will be apparent to those skilled in the art that other combinations can be utilized as desired without departing from the scope of the invention.

FIG. 9 illustrates a schematic diagram of an intravenous fluid delivery system 900 utilizing differential force sensors such as sensor 200, 500, 600 and 800 on either side of the orifice 910 for monitoring manual injections, which can be implemented in accordance with a preferred embodiment. The intravenous fluid delivery system 900 includes an intravenous tube 920 and an injection point 930 for delivering medications to a patient, as illustrated by arrow 950. The differential force sensor such as sensor 200, 500, 600 and 800, which includes piezoresistive sense die 140, can be placed on either side of the orifice 910 for measuring differential force on either side of the orifice 910. The piezoresistive sense die 140 can be utilized to measure forces F1 and F2 exerted on the diaphragm 415 on either side of the orifice 910. The piezoresistive sense die 140 can be packaged in close proximity to make intimate contact with the diaphragm(s) 415 located on either side of the orifice 910.

The intravenous medications such as, for example, antibiotics, antivirals, antiemetics, chemotherapy, and biotechnology drugs can be administrated intermittently with a frequency through the injection point 930. Depending on the frequency of administration, the patient is either repeatedly connected to and disconnected from the intravenous line or is continuously connected to the intravenous line between administrations. The differential force sensor such as sensor 200, 500, 600 and 800 can be mounted very close to the point of entry into the patient's body. Such differential force sensor such as sensor 200, 500, 600 and 800 is capable of automatically monitoring manual injections through the intravenous line 920. The output of the sensor can be the individual force measurements in the form of an electrical signal (either digital or analog) and potentially a differential signal (the difference between the two sense elements). Such small size and lightweight differential force sensor for monitoring manual injections through the intravenous line 920 reduce patient discomfort.

Such differential force sensor 200, 500, 600 and 800 is a high-performance transducer specifically designed to address the needs of medical and specialized OEM (original equipment manufacturer) applications. The differential force sensor 200, 500, 600, and 800 can be specified to operate with either a constant current or voltage supply. Each force sensor 200, 500, 600 and 800 employs a solid-state piezo-resistive pressure transducer mounted in a plastic package. Such an approach provides a reliable solution for applications where force can be applied by a flexible membrane to the sensor, such as that found in infusion pumps. The differential force also provides access to important safety features in critical care medical instrumentation such as occlusion pressure or infiltration detection. The pressure data can provide medical personnel with useful diagnostic information regarding the condition of the patient's circulatory system. The differential force sensor can also be utilized with other medical dispensing devices, such as syringe pumps, to improve safety and accuracy.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. An apparatus for monitoring fluid flow through a fluid line having a reduced cross-section orifice along the length of the fluid line, comprising:
   a first sense die and a second sense die positioned adjacent to one another in a common sensor package, wherein said first sense die is responsive to movement of a first flow diaphragm that is exposed to a first pressure in the fluid line upstream of the reduced cross-section orifice, and said second sense die is responsive to movement of a second flow diaphragm that is exposed to a second pressure in the fluid line downstream of the reduced cross-section orifice.

2. The apparatus of claim 1 further comprising:
   a first plunger associated with the first sense die, wherein a first force exerted by movement of said first flow diaphragm in response to said first pressure is transferred to said first sense die through said first plunger; and
   a second plunger associated with the second sense die, wherein a second force exerted by movement of said second flow diaphragm in response to said second pressure is transferred to said second sense die through said second plunger.

3. The apparatus of claim 1 wherein:
   each of said first sense die and said second sense die is placed between a conductive seal stack; and
   said conductive seal stack is positioned on a printed circuit board held captive by the common sensor package.

4. The apparatus of claim 3 wherein said conductive seal stack comprises at least one of the following: an environmental seal and a conductive seal.

5. The apparatus of claim 1 wherein:
   each of the first sense die and said second sense die is fixed relative to a printed circuit board of the common sensor package;
   a housing of said common sensor package is located over said first sense die and said second sense die; and
   said common sensor package further includes:
      a first sensor orifice positioned directly above said first sense die;
      a second sensor orifice positioned directly above said second sense die; and
      a gel dispensed into said first sensor orifice and said second sensor orifice.

6. The apparatus of claim 5 further comprising:
   a first plunger associated with the first sense die, wherein a first force exerted by movement of said first flow diaphragm is transferred to said first sense die through said first plunger and said gel in said first sensor orifice; and
   a second plunger associated with the second sense die, wherein a second force exerted by movement of said second flow diaphragm is transferred to said second sense die through said second plunger and said gel in said second sensor orifice.

7. The apparatus of claim 1 further comprising:
   a carrier, wherein said first sense die and said second sense die are glued to said carrier;
   at least one orifice formed in said carrier, wherein a gel is dispensed into said at least one orifice in order to allow said gel to make intimate contact with an etched side of said first sense die and said second sense die; and
   a cover located over said carrier to maintain said first flow diaphragm and said first flow diaphragm in place relative to said at least one orifice formed in said carrier.

8. The apparatus of claim 7 wherein said carrier is fixed to a printed circuit board of the common sensor housing.

9. The apparatus of claim 1 further comprising:
   at least one electrical component electrically connected to receive one or more sensor signals from said first sense die and said second sense die, said at least one electrical component is configured to perform a differential pressure calculation using the one or more sensor signals from said first sense die and said second sense die.

10. The apparatus of claim 1 further comprising:
    at least one electrical component electrically connected to receive one or more sensor signals from said first sense die and said second sense die, said at least one electrical component is configured to perform a signal compensation of the one or more sensor signals.

11. An apparatus for monitoring fluid flow through a fluid line having a reduced cross-section orifice along the length of the fluid line, comprising:
    a first sense die and a second sense die positioned adjacent to one another and fixed to a common substrate, wherein said first sense die is responsive to movement of a first flow diaphragm that is exposed to a first pressure in the fluid line upstream of the reduced cross-section orifice, and said second sense die is responsive to movement of a second flow diaphragm that is exposed to a second pressure in the fluid line downstream of the reduced cross-section orifice.

12. The apparatus of claim 11 wherein:
    each of the first sense die and said second sense die is fixed relative to a printed circuit board;
    a housing is located over said first sense die and said second sense die;
    a first sensor orifice is positioned directly above said first sense die;
    a second sensor orifice is positioned directly above said second sense die; and
    a gel is dispensed into said first sensor orifice and said second sensor orifice.

13. The apparatus of claim 12 further comprising:
    a first plunger associated with the first sense die, wherein a first force exerted by movement of said first flow diaphragm is transferred to said first sense die through said first plunger and said gel in said first sensor orifice; and
    a second plunger associated with the second sense die, wherein a second force exerted by movement of said second flow diaphragm is transferred to said second sense die through said second plunger and said gel in said second sensor orifice.

14. The apparatus of claim 11 further comprising:
    at least one electrical component electrically connected to receive one or more sensor signals from said first sense die and said second sense die, wherein said at least one electrical component is configured to perform a differential pressure calculation using the one or more sensor signals from said first sense die and said second sense die.

15. The apparatus of claim 11 further comprising:
    at least one electrical component electrically connected to receive one or more sensor signals from said first sense die and said second sense die, said at least one electrical component is configured to perform a signal compensation of the one or more sensor signals.

16. A method for monitoring fluid flow through a fluid line having a reduced cross section orifice along the length of the fluid line, comprising:
    providing a package that includes a first sense die and a second sense die positioned adjacent to one another, wherein said first sense die is responsive to movement of a first flow diaphragm that is exposed to a first pressure in the fluid line upstream of the reduced cross-section orifice, and said second sense die is responsive to movement of a second flow diaphragm that is exposed to a second pressure in the fluid line downstream of the reduced cross-section orifice; and transferring a first force exerted by movement of said first flow diaphragm in response to said first pressure to said first sense die, and transferring a second force exerted by movement of said second flow diaphragm in response to said second pressure to said second sense die.

17. The method of claim 16 further comprising:

performing signal processing utilizing at least one electronic device associated with said first sense die and said second sense die, wherein said signal processing includes performing a thermal compensation and/or a differential pressure calculation.

18. The method of claim 16, wherein the force is transferred from said first flow diaphragm to said first sense die through a first plunger, and the force is transferred from said second flow diaphragm to said second sense die through a second plunger.

19. The method of claim 16, wherein the force is transferred from said first flow diaphragm to said first sense die through a first gel element, and the force is transferred from said second flow diaphragm to said second sense die through a second gel element.

20. The method of claim 16 further comprising communicating one or more signals related to the fluid flow through the fluid line to electronics external to the package.

* * * * *